(12) United States Patent
Fish et al.

(10) Patent No.: US 7,083,839 B2
(45) Date of Patent: Aug. 1, 2006

(54) LAMINATE STRUCTURES CONTAINING ACTIVATABLE MATERIALS

(75) Inventors: Jeffrey E. Fish, Dacula, GA (US); Michael S. Brunner, Roswell, GA (US); Naveen Agarwal, Atlanta, GA (US); Laura Folkenberg, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 182 days.

(21) Appl. No.: 10/027,261

(22) Filed: Dec. 20, 2001

(65) Prior Publication Data

US 2003/0118779 A1 Jun. 26, 2003

(51) Int. Cl.
*A61F 7/00* (2006.01)

(52) U.S. Cl. .................. 428/35.7; 607/96; 607/117
(58) Field of Classification Search ............ 428/35.7, 428/34.1, 321.1; 607/96, 114
See application file for complete search history.

(56) References Cited

U.S. PATENT DOCUMENTS

| | | | |
|---|---|---|---|
| 1,025,012 A | 4/1912 | Norwood | |
| 1,313,021 A | 8/1919 | Scott | |
| 1,897,025 A | 2/1933 | Palmer | |
| 2,435,637 A | 2/1948 | Sevush | |
| 2,583,381 A | 1/1952 | Leguillon | |
| 3,338,992 A | 8/1967 | Kinney | |
| 3,341,394 A | 9/1967 | Kinney | |
| 3,502,538 A | 3/1970 | Peterson | |
| 3,502,763 A | 3/1970 | Hartmann | |
| 3,542,615 A | 11/1970 | Dobo et al. | |
| 3,687,143 A | 8/1972 | Schneeberger et al. | |
| 3,692,618 A | 9/1972 | Dorschner et al. | |
| 3,756,389 A | 9/1973 | Firth | |
| 3,763,622 A | 10/1973 | Stanley, Jr. | |
| 3,802,817 A | 4/1974 | Matsuki et al. | |
| 3,849,241 A | 11/1974 | Butin et al. | |
| 3,855,046 A | 12/1974 | Hansen et al. | |
| 3,874,504 A | 4/1975 | Verakas | |
| 3,900,035 A | 8/1975 | Welch et al. | |
| 3,929,131 A | 12/1975 | Hardwick | |
| 3,935,355 A | * 1/1976 | Kuhn | ............ 24/150 R |
| 4,041,203 A | 8/1977 | Brock et al. | |

(Continued)

FOREIGN PATENT DOCUMENTS

| | | |
|---|---|---|
| EP | 0613357 B1 | 1/1997 |
| WO | WO 01/03625 A2 | 1/2001 |
| WO | WO 01/87589 A2 | 11/2001 |
| WO | WO 01/88245 A2 | 11/2001 |

OTHER PUBLICATIONS

SANI–WIPE—EPA Pesticide Registration,—Form 9570–6, Reg. #9480–7, Dated Apr. 5, 2001.
Search Report PCT/US02/28325, Feb. 2003.
U.S. Appl. No. 00/92,199, Fish, et al., filed Jul. 18, 2002.

(Continued)

*Primary Examiner*—Sandra M. Nolan
(74) *Attorney, Agent, or Firm*—Dority & Manning, P.A.

(57) ABSTRACT

A laminate structure (e.g., hot or cold wrap) formed from outer substrates that are bonded together to form at least one pocket is provided. The pocket is separated by an inner substrate such that the pocket defines an upper pocket region and a lower pocket region, each of which contains a reactant. Due to the presence of the inner substrate, the reactants do not intermix prior to activation of the laminate structure. To activate the laminate structure, a tension force is exerted so that the inner substrate ruptures, thereby allowing the reactants to freely intermix and produce the desired result. For example, in some instances, the reactants undergo and exothermic or endothermic reaction so that the laminate structure may be utilized as a hot or cold wrap.

34 Claims, 2 Drawing Sheets

U.S. PATENT DOCUMENTS

| | | |
|---|---|---|
| 4,055,188 A | 10/1977 | Pelton |
| 4,057,047 A | 11/1977 | Gossett |
| 4,081,256 A | 3/1978 | Donnelly |
| 4,205,685 A | 6/1980 | Yoshida et al. |
| 4,230,105 A | 10/1980 | Harwood |
| 4,255,157 A | 3/1981 | Yamaguchi et al. |
| 4,268,272 A | 5/1981 | Taura |
| 4,282,005 A | 8/1981 | Sato et al. |
| 4,323,534 A | 4/1982 | DesMarais |
| 4,340,563 A | 7/1982 | Appel et al. |
| 4,347,848 A | 9/1982 | Hubbard et al. |
| 4,366,804 A | 1/1983 | Abe |
| 4,374,888 A | 2/1983 | Bornslaeger |
| 4,385,950 A | 5/1983 | Hubbard et al. |
| 4,397,315 A | 8/1983 | Patel |
| 4,408,643 A | 10/1983 | Laske et al. |
| 4,427,010 A | 1/1984 | Marx |
| 4,462,224 A | 7/1984 | Dunshee et al. |
| 4,527,566 A | 7/1985 | Abare |
| RE32,026 E | 11/1985 | Yamashita et al. |
| 4,575,097 A | 3/1986 | Brannigan et al. |
| 4,586,506 A | 5/1986 | Nangle |
| 4,649,895 A | 3/1987 | Yasuki et al. |
| 4,652,487 A | 3/1987 | Morman |
| 4,655,760 A | 4/1987 | Morman et al. |
| 4,657,802 A | 4/1987 | Morman |
| 4,663,220 A | 5/1987 | Misneski et al. |
| 4,676,247 A | 6/1987 | Van Cleve |
| 4,685,944 A | 8/1987 | Allan et al. |
| 4,688,572 A | 8/1987 | Hubbard et al. |
| 4,720,415 A | 1/1988 | Vander Wielen et al. |
| 4,724,184 A | 2/1988 | Killian et al. |
| 4,747,841 A | 5/1988 | Kuratomi et al. |
| 4,753,241 A | 6/1988 | Brannigan et al. |
| 4,756,299 A | 7/1988 | Podella |
| 4,766,029 A | 8/1988 | Brock et al. |
| 4,780,117 A | 10/1988 | Lahey et al. |
| 4,781,966 A | 11/1988 | Taylor |
| 4,789,699 A | 12/1988 | Kieffer et al. |
| 4,803,117 A | 2/1989 | Daponte |
| 4,805,620 A | 2/1989 | Meistrell |
| 4,820,572 A | 4/1989 | Killian et al. |
| 4,828,556 A | 5/1989 | Braun et al. |
| 4,834,738 A | 5/1989 | Kielpikowski et al. |
| 4,856,651 A | 8/1989 | Francis, Jr. |
| 4,886,063 A | 12/1989 | Crews |
| 4,891,501 A | 1/1990 | Lipton |
| 4,898,592 A | 2/1990 | Latzke et al. |
| 4,902,248 A | 2/1990 | Robertson |
| 4,911,707 A | 3/1990 | Heiber et al. |
| 4,923,742 A | 5/1990 | Killian et al. |
| 4,925,743 A | 5/1990 | Ikeda et al. |
| 4,946,290 A | 8/1990 | Matyja |
| 4,951,666 A | 8/1990 | Inman et al. |
| 4,953,550 A | 9/1990 | Dunshee |
| 4,963,360 A | 10/1990 | Argaud |
| 4,965,122 A | 10/1990 | Morman |
| 4,981,747 A | 1/1991 | Morman |
| 4,986,076 A | 1/1991 | Kirk et al. |
| 4,995,217 A | 2/1991 | Francis, Jr. |
| 5,016,629 A | 5/1991 | Kanare |
| 5,020,711 A | 6/1991 | Kelley |
| 5,046,479 A | 9/1991 | Usui |
| 5,074,300 A | 12/1991 | Murphy |
| 5,093,422 A | 3/1992 | Himes |
| 5,109,841 A | 5/1992 | Hubbard et al. |
| 5,114,781 A | 5/1992 | Morman |
| 5,116,662 A | 5/1992 | Morman |
| 5,125,392 A | 6/1992 | Hardwick |
| 5,169,706 A | 12/1992 | Collier, IV et al. |
| 5,211,949 A | 5/1993 | Salyer |
| 5,213,881 A | 5/1993 | Timmons et al. |
| 5,215,080 A | 6/1993 | Thomas et al. |
| 5,226,992 A | 7/1993 | Morman |
| 5,304,216 A | 4/1994 | Wallace |
| 5,304,599 A | 4/1994 | Himes |
| 5,332,613 A | 7/1994 | Taylor et al. |
| 5,336,545 A | 8/1994 | Morman |
| 5,342,412 A | 8/1994 | Ueki |
| 5,356,426 A | 10/1994 | Delk et al. |
| 5,366,793 A | 11/1994 | Fitts, Jr. et al. |
| 5,374,919 A | 12/1994 | Zelka et al. |
| 5,382,400 A | 1/1995 | Pike et al. |
| 5,385,775 A | 1/1995 | Wright |
| 5,395,399 A | 3/1995 | Rosenwald |
| 5,425,725 A | 6/1995 | Tanzer et al. |
| 5,431,622 A | 7/1995 | Pyrozyk et al. |
| 5,433,715 A | 7/1995 | Tanzer et al. |
| 5,464,688 A | 11/1995 | Timmons et al. |
| 5,466,251 A | 11/1995 | Brunson et al. |
| 5,503,908 A | 4/1996 | Faass |
| 5,507,794 A | 4/1996 | Allen |
| 5,514,470 A | 5/1996 | Haffner et al. |
| 5,545,197 A | 8/1996 | Bowen |
| 5,572,744 A | 11/1996 | Ried, Jr. et al. |
| 5,591,510 A | 1/1997 | Junker et al. |
| 5,593,399 A | 1/1997 | Tanzer et al. |
| 5,604,959 A | 2/1997 | Bowen |
| 5,620,779 A | 4/1997 | Levy et al. |
| 5,641,325 A | 6/1997 | Delk et al. |
| 5,658,583 A | 8/1997 | Zhang et al. |
| 5,662,624 A | 9/1997 | Sundstrom et al. |
| 5,700,531 A | 12/1997 | Gillberg-LaForce et al. |
| D390,708 S | 2/1998 | Brown |
| 5,723,002 A | 3/1998 | Delk et al. |
| 5,741,318 A | 4/1998 | Ouellette et al. |
| 5,792,213 A | 8/1998 | Bowen |
| 5,805,620 A | 9/1998 | Liu et al. |
| 5,817,145 A | 10/1998 | Augustine et al. |
| 5,837,005 A | 11/1998 | Viltro et al. |
| 5,906,637 A | 5/1999 | Davis et al. |
| 5,925,072 A | 7/1999 | Cramer et al. |
| 5,962,112 A | 10/1999 | Haynes et al. |
| 5,962,117 A | 10/1999 | Furutani et al. |
| 5,967,308 A | 10/1999 | Bowen |
| 5,984,995 A | 11/1999 | White |
| 6,020,040 A | 2/2000 | Cramer et al. |
| 6,036,004 A | 3/2000 | Bowen |
| 6,071,254 A | 6/2000 | Augustine |
| 6,071,304 A | 6/2000 | Augustine et al. |
| 6,074,413 A | 6/2000 | Davis et al. |
| D428,267 S | 7/2000 | Romano, III et al. |
| 6,093,665 A | 7/2000 | Sayovitz et al. |
| 6,099,556 A | 8/2000 | Usui |
| 6,102,937 A | 8/2000 | Cramer et al. |
| 6,103,139 A | 8/2000 | Kohout |
| 6,146,732 A | 11/2000 | Davis et al. |
| 6,149,638 A | 11/2000 | Vogt et al. |
| 6,156,421 A | 12/2000 | Stopper et al. |
| 6,158,427 A | 12/2000 | McGuire et al. |
| 6,248,125 B1 | 6/2001 | Helming |
| 6,289,889 B1 | 9/2001 | Bell et al. |
| 6,336,935 B1 | 1/2002 | Davis et al. |
| 6,361,553 B1 | 3/2002 | Bowen |
| 6,582,383 B1 | 6/2003 | Horning |

OTHER PUBLICATIONS

U.S. Appl. No. 00/95,127, Fish, et al., filed Jul. 18, 2002.
U.S. Appl. No. 01/02,392, Fish, et al., filed Aug. 1, 2002.
U.S. Appl. No. 01/24,277, Agarwal, et al., filed Jul. 3, 2003.
U.S. Appl. No. 00/65,315, Fish, et al., filed Mar. 8, 2004.

U.S. Appl. No. 01/16,023, Huang, et al., filed Jun. 17, 2004.
U.S. Appl. No. 01/16,990, Agarwal, et al., filed Jun. 17, 2004.
U.S. Appl. No. 01/86,540, Agarwal, et al., filed Sep. 23, 2004.
U.S. Appl. No. 01/86.541. Agarwal, et al., filed Sep. 23, 2004.
Abstract–Asahi Chem Ind Co Ltd, JP55005940, Jan. 17, 1980.

Drawing–Matsushita Electric Ind Co LTD, JP56001150, Jan. 8, 1981.

Abstract–Tsurumi Sooda KK, JP57162775, Oct. 6, 1982.

Abstract–Akiyoshi Kataoka, JP21744861, Jul. 6, 1990.

Abstract–Fabritz Gerhard, DE4005718, Sep. 13, 1990.

* cited by examiner

LAMINATE STRUCTURES CONTAINING ACTIVATABLE MATERIALS

BACKGROUND OF THE INVENTION

Thermal wraps or packs are commonly used to treat various injuries and ailments. For instance, cold packs, which typically decrease blood flow, are often used to reduce swelling and pain. Hot packs, which typically increase blood flow, are often used to warm muscles or reduce cramping. Conventional hot and cold packs are generally of two types: those that require external heating or cooling, and "chemical packs" that mix two or more reactants to cause an endothermic or exothermic reaction.

The chemical packs generally come in two varieties: the bag-in-bag type or the side-by-side type. The bag-in-bag type wrap has two separate bags, with a smaller bag containing one of the reactants included within the larger bag that contains the other reactant. Bag-in-bag chemical packs suffer from the significant disadvantage that there is a large surface area, represented by the exterior surface of the smaller bag, between the first reactant and the second reactant. Here, if a reactant is a liquid or gas, it will migrate through the plastic material of the smaller bag and into the second reactant causing a pre-activation intermixing of the reactants that results in a short shelf life and a lower efficiency upon intentional activation. This migration through the smaller bag can be slowed by using a thicker plastic material for the smaller bag; however, when a thicker smaller bag is utilized, it becomes more difficult to activate the pack when activation is desired. Also, with the bag-in-bag design, it is sometimes difficult to rupture the smaller bag. A number of prior art devices have utilized a rigid spike to facilitate rupturing the smaller bag. This presents significant shortcomings in that the rigid spike may puncture the larger bag in use or in shipping and handling causing external leaking.

The side-by-side bags utilize a breakable seal between two compartments located side-by-side, each compartment containing one of the reactants. These side-by-side packs attempt to utilize a strong seal around the perimeter of the bag and a weak seal to separate the two compartments. This is very difficult to do on a consistent basis and with known manufacturing techniques and leads to a situation where a force, intended to mix the two reactants, breaks an exterior seal causing a leak of the reactants onto the potential user.

As such, a need continues to exist for a hot or cold wrap or pack that is relatively easy to activate.

SUMMARY OF THE INVENTION

In accordance with one embodiment of the present invention, a laminate structure is disclosed that includes an inner substrate that ruptures upon the application of a certain tensile force in a longitudinal direction. In some embodiments, the inner substrate is selected from the group consisting of nonwoven webs, films, woven fabrics, knitted fabrics and combinations thereof. For example, in one embodiment, the inner substrate contains a film and/or a nonwoven web.

The laminate structure also includes a first outer substrate and a second outer substrate. In some embodiments, the first and said second substrates are selected from the group consisting of nonwoven webs, films, woven fabrics, knitted fabrics and combinations thereof. For example, in one embodiment, the outer substrates contain a film and/or a nonwoven web.

To better ensure that the outer substrates do not substantially rupture upon application of the tensile force, the outer substrates are generally extensible in the direction that the tensile force is. In some embodiments, the substrate(s) can extend in the longitudinal direction at least about 30%, in some embodiments at least about 50%, and in some embodiments, at least about 75% upon application of the tensile force. For example, in one embodiment, the substrate can contain an elastomeric material to enhance its extensibility. In another embodiment, the substrate can have a length greater than the length of the inner substrate such that it can be folded and thereby become more extensible.

The inner substrate is positioned between and bonded to the first and second outer substrates to define at least one pocket having an upper pocket region and a lower pocket region. For example, in some embodiments, two longitudinal edges and one transverse edge of the first substrate and second substrate are bonded together. Further, the inner substrate can be bonded to the two longitudinal edges of the first and second substrates. In such instances, the inner substrate may, if desired, remain unbonded to an additional transverse edge of the first and second substrates.

A first reactant is contained within the upper pocket region of the pocket and a second reactant is contained within the lower pocket region of the pocket. Thus, when the inner substrate ruptures, the reactants intermix and can, for example, undergo an endothermic or exothermic reaction.

In some embodiments, the laminate structure comprises multiple pockets. If desired, the multiple pockets may be aligned in series.

In accordance with another embodiment of the present invention, a method for heating or cooling a body part of a user is disclosed that includes providing a wrap that comprises an inner substrate and extensible first and second outer substrates. The inner substrate is positioned between and bonded to the first and second outer substrates to define multiple pockets aligned in series. Each of the pockets has an upper pocket region and a lower pocket region. In addition, a first reactant is contained within the upper pocket region of at least a portion of the pockets and a second reactant is contained with the lower pocket region of at least a portion of the pockets.

The method also includes stretching the wrap in a longitudinal direction until the inner substrate ruptures. The rupturing of the inner substrate causes the reactants to intermix and undergo an endothermic or exothermic reaction. The first and second outer substrates remain substantially unruptured based on their extensibility. Once activated in this manner, the wrap can then be applied to the body part for the desired heating or cooling effect.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
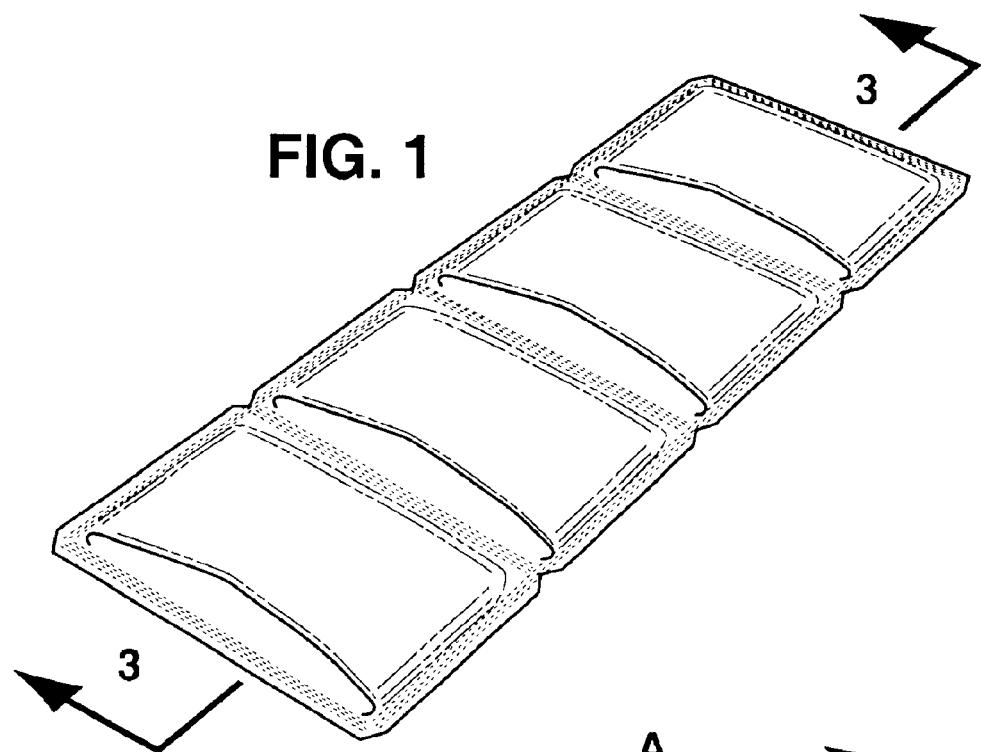
FIG. 1 is a perspective view of one embodiment of a laminate structure of the present invention.

Repeat use of reference characters in the present specification and drawings is intended to represent same or analogous features or elements of the invention.

DETAILED DESCRIPTION OF REPRESENTATIVE EMBODIMENTS

Definitions

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, bonded carded web processes, etc. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein the term "microfibers" means small diameter fibers having an average diameter not greater than about 75 microns, for example, having an average diameter of from about 0.5 microns to about 50 microns, or more particularly, microfibers may have an average diameter of from about 2 microns to about 40 microns.

As used herein, the term "meltblown fibers" refers to fibers formed by extruding a molten thermoplastic material through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that may be continuous or discontinuous, are generally smaller than 10 microns in diameter, and are generally tacky when deposited onto a collecting surface.

As used herein, the term "spunbonded fibers" refers to small diameter substantially continuous fibers that are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spun-bonded nonwoven webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are incorporated herein in their entirety by reference thereto for all purposes. Spunbond fibers are generally not tacky when they are deposited onto a collecting surface. Spunbond fibers can sometimes have diameters less than about 40 microns, and are often between about 5 to about 20 microns.

As used herein, the phrase "bonded carded web" refers to webs that are made from staple fibers which are sent through a combing or carding unit, which separates or breaks apart and aligns the staple fibers to form a nonwoven web. Once the web is formed, it then is bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface if so desired. Another suitable and well-known bonding method, particularly when using bicomponent staple fibers, is through-air bonding.

As used herein, the phrase "point unbonded" or "pattern unbonded" generally refers to a fabric having continuous thermally bonded areas defining a plurality of discrete unbonded areas. The fibers within the discrete unbonded areas are dimensionally stabilized by the continuous bonded areas that encircle or surround each unbonded area. The unbonded areas are specifically designed to afford spaces between fibers or filaments within the unbonded areas. A suitable process for forming point-unbonded nonwoven materials are described in U.S. Pat. No. 5,962,117, which is incorporated herein in its entirety by reference thereto for all purposes. For example, the process can include passing a heated nonwoven fabric (e.g., nonwoven web or multiple nonwoven web layers) between calendar rolls, with at least one of the rolls having a bonding pattern on its outermost surface comprising a continuous pattern of land areas defining a plurality of discrete openings, apertures, or holes. Each of the openings in the roll (or rolls) defined by the continuous land areas forms a discrete unbonded area in at least one surface of the resulting nonwoven fabric in which the fibers are substantially or completely unbonded. Alternative embodiments of the process include pre-bonding the nonwoven fabric or web before passing the fabric or web within the nip formed by the calender rolls.

As used herein, the phrase "point bonded" or "thermal point bonded" generally refers to a fabric (e.g., fibrous web or multiple fibrous web layers) or webs to be bonded between heated rolls. One roll is usually patterned in some way so that the entire fabric is not bonded across its entire surface, and the other roll is usually smooth. As a result, various patterns for calendar rolls have been developed for functional as well as aesthetic reasons. One example of a pattern that has points is the Hansen-Pennings or "H&P" pattern with about a 30% bond area with about 200 pins/square inch as taught in U.S. Pat. No. 3,855,046 to Hansen, which is incorporated herein in its entirety by reference thereto for all purposes. The H&P pattern has square point or pin bonding areas. Another typical point bonding pattern is the expanded Hansen-Pennings or "EHP" bond pattern which produces a 15% bond area. Another typical point bonding pattern designated "714" has square pin bonding areas wherein the resulting pattern has a bonded area of about 15%. Other common patterns include a diamond pattern with repeating and slightly offset diamonds with about a 16% bond area and a wire weave pattern looking as the name suggests, e.g. like a window screen, with about an 18% bond area. Other exemplary bond patterns include, but are not limited to, those described in U.S. Pat. No. 5,620,779 to Levy, et al., U.S. Pat. No. 5,962,112 to Haynes, et al., U.S. Pat. No. 6,093,665 to Sayovitz, et al., U.S. Design Pat. No. 428,267 to Romano, et al. and U.S. Design Pat. No. 390,708 to Brown, which are incorporated herein in their entirety by reference thereto for all purposes.

As used herein, "through air bonding" or "TAB" means a process of bonding a nonwoven, for example, a multicomponent fiber web, in which air which is sufficiently hot to melt one of the polymers of which the fibers of the web are made is forced through the web. The melting and resolidification of the polymer provides the bonding.

As used herein, "ultrasonic bonding" means a process performed, for example, by passing the fabric between a sonic horn and anvil roll as illustrated in U.S. Pat. No. 4,374,888 to Bornslaeger, which is incorporated herein in its entirety by reference thereto for all purposes.

As used herein, the term "fiber" refers to an elongated extrudate formed by passing a polymer through a forming orifice such as a die. Unless noted otherwise, the term "fibers" includes discontinuous strands having a definite length and continuous strands of material, such as filaments.

As used herein, the term "reactants" refers to materials that are capable of physically and/or chemically interacting in some manner when intermixed. For example, the reactants can physically interact such that their physical form is altered in some manner (e.g., cement and water, plaster of paris and water, flour and water, epoxy and hardener, medicament dissolved in water, etc.). In other instances, one of the reactants may simply combine with the other reactant without changing its physical form (e.g., saturation of a dry material with water, such as a cotton swab and medicament). The reactants may also chemically interact, such as reacting to produce a certain product (e.g., heat; gases, such as reacting baking soda and vinegar to produce carbon dioxide gas; etc.).

DETAILED DESCRIPTION

Reference now will be made in detail to various embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention covers such modifications and variations as come within the scope of the appended claims and their equivalents.

In general, the present invention is directed to a laminate structure formed from outer extensible substrates that are bonded together to form at least one pocket. The pocket is separated by an inner substrate such that the pocket defines an upper pocket region and a lower pocket region, each of which contain a reactant. Due to the presence of the inner substrate, the reactants do not intermix prior to activation of the laminate structure. To activate the laminate structure, a tension force is exerted so that the inner substrate ruptures, thereby allowing the reactants to freely intermix and produce the desired result.

For example, referring to FIGS. 1–4, one embodiment of a laminate structure of the present invention is illustrated. As shown, the structure 10 includes two outer substrates 12 and 14 that define four (4) pockets 22. When containing multiple pockets, the laminate structure may provide the desired effect (e.g., heating, cooling, etc.) over a greater surface area. However, it should be understood that any number of pockets may be utilized, so long as at least one pocket is present within the laminate structure.

The pockets 22 may have any desired size or shape. For example, the pocket 22 may have the shape of a circle, oval, square, rectangle, hexagon, etc. Moreover, in some instances, the boundaries for length, width, and height of the pocket 22 can fall within a certain range such that the pocket 22 is relatively small and allows flexibility of the resulting laminate structure 10. For example, in some embodiments, the length "l" of the pocket 22 is less than about 20 centimeters, and in some embodiments, between about 0.5 centimeters to about 10 centimeters. Moreover, in some embodiments, the height "h" of the pocket 22 is less than about 5 centimeters, and in some embodiments, between about 0.1 centimeters to about 1 centimeter. Further, in some embodiments, the width "w" of the pocket 22 is less than about 20 centimeters, and in some embodiments, between about 0.5 centimeters to about 10 centimeters. It should be understood, however, that the pockets 22 need not have the same size or shape.

Moreover, the pockets 22 may generally be arranged and/or spaced apart in any manner desired. For example, in one particular embodiment, as shown in FIGS. 1–4, the pockets 22 are aligned in series. When aligned in series, the approximate distance "x" that the pockets 22 are spaced apart is equal to or less than five (5) times the length "l" of the pocket 22, and in some embodiments, equal to or less than the length "l" of the pocket 22. For example, in some embodiments, the distance "x" can be less than about 100 centimeters, in some embodiments, less than about 50 centimeters, in some embodiments, less than about 20 centimeters, and in some embodiments, less than about 10 centimeters. However, it should be understood that, in certain instances, the pockets 22 may be separated by a relatively large distance. For example, the pockets 22 may be separate a string or other similar device that enables interlinks the pockets over any desired distance.

If desired, the pockets 22 may also be aligned in two or more directions such that the resulting laminate structure 10 is multi-dimensional. When aligned in multiple dimensions, the distance separating the pockets 22 can be the same as described above. Although various dimensions have been set forth above, it should be understood that other dimensions are also contemplated in the present invention. For instance, the particular pocket dimensions may vary depending on the overall dimensions of the laminate structure. Moreover, it should also be understood that the dimensions set forth above are approximate "maximum" dimensions for a given direction. Thus, a pocket having a certain approximate height, for example, may have other heights at different locations in the width direction of the pocket. In some instances, some of the heights of a pocket may actually exceed the given dimension.

Figure 2:
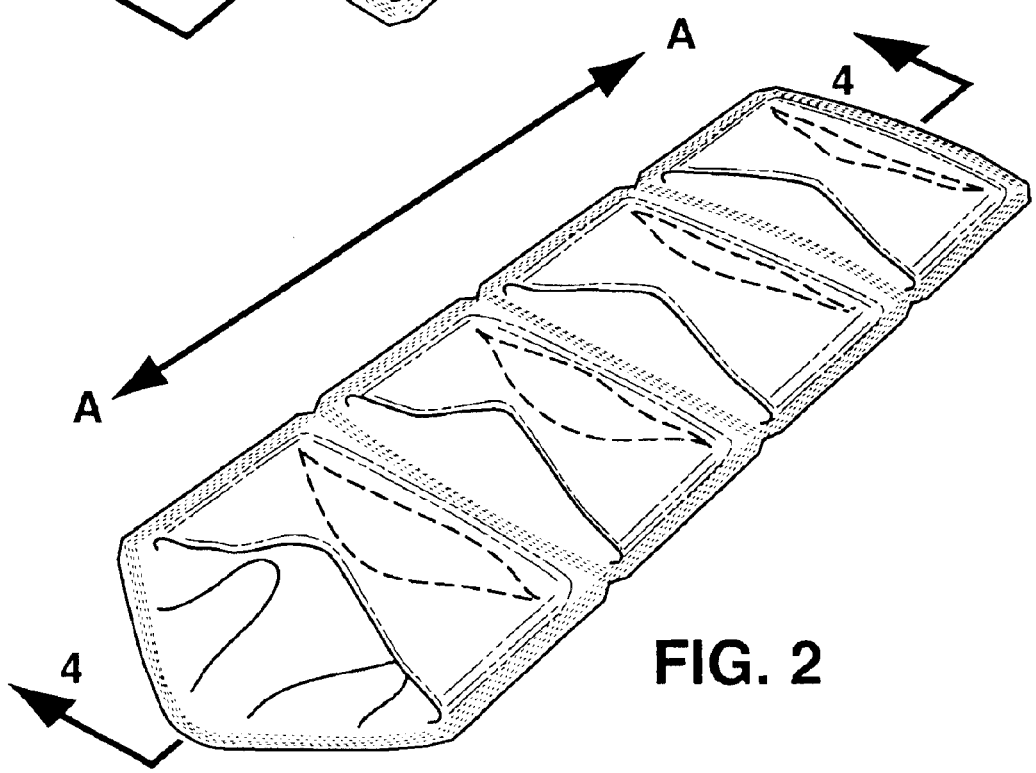
FIG. 2 is a perspective view of the laminate structure of FIG. 1 with a ruptured inner substrate.
Figure 3:
FIG. 3 is a cross-sectional view of the laminate structure of FIG. 1 taken along a line 3—3.
Figure 4:
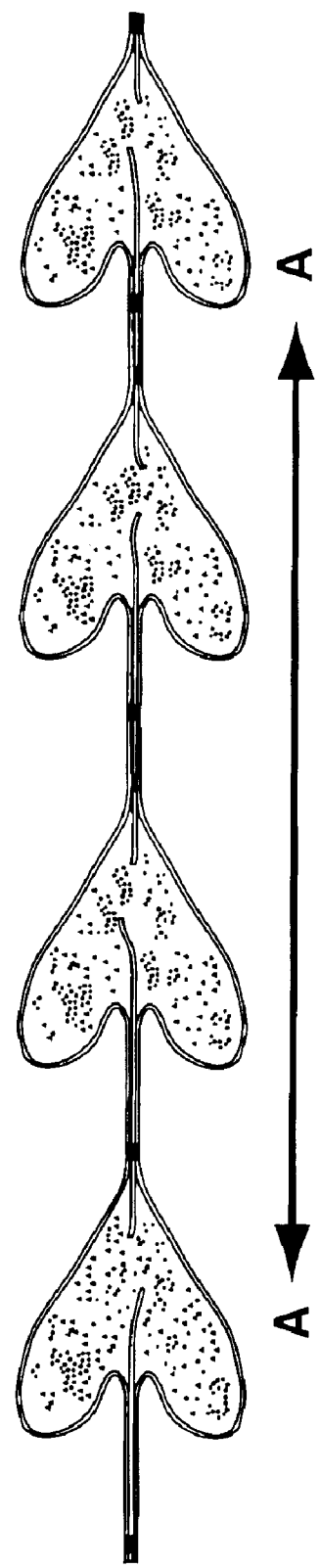
FIG. 4 is a cross-sectional view of the laminate structure of FIG. 2 taken along a line 4—4.

Referring again to FIGS. 1–4, an inner substrate 16 is also positioned between and bonded to the outer substrates 12 and 14. In one embodiment, as shown, bonds 48 and 50 are formed between the inner substrate 16 and outer substrates 12 and 14 at the longitudinal edges 61. Besides being bonded together by the bonds 48 and 50, bonds 49 are also formed between the inner substrate 16 and outer substrates 12 and 14. In one embodiment, as shown, a bond 52 is also formed at one transverse edge 65. The substrates remains at the other transverse edge 67. As a result of such selective bonding, the inner substrate 16 is relatively free to be stretched and moved in the longitudinal direction "l" of the structure 10, as illustrated in FIGS. 2 and 4.

Any bonding method may generally be utilized in the present invention to bond together the materials of the laminate structure. For instance, thermal bonding techniques, such as thermal point bonding, pattern unbending, etc., through-air bonding, and ultrasonic bonding are some examples of techniques that may be utilized. In addition, other bonding methods, such as adhesive bonding, etc., may also be utilized. For example, some suitable adhesives are described in U.S. Pat. No. 5,425,725 to Tanzer, et al.; U.S. Pat. No. 5,433,715 to Tanzer, et al.; and U.S. Pat. No. 5,593,399 to Tanzer, et al., which are incorporated herein in their entirety by reference thereto for all purposes.

Referring again to FIGS. 1–4, one or more of the pockets 22 define an upper pocket region 24 containing a first reactant 32 and a lower pocket region 26 containing a second reactant 34. It should be understood, however, that all of the pockets 22 need not contain reactants. Moreover, when utilizing multiple pockets, some of the pockets may contain one type of reactants, while other pockets may contain a different type of reactants.

The reactants 32 and 34 can generally be any suitable solid, liquid, gas, or combinations thereof. For instance, when the structure 10 is used as a hot or cold chemical wrap, the reactants 32 and 34 can contain materials that undergo an exothermic or endothermic reaction when intermixed.

In one embodiment, for example, water and ammonium nitrate ($NH_4NO_3$), which are known to endothermically react when intermixed, can be used. In this embodiment, water would be held in one pocket region, for illustrative purposes, the upper pocket region 22, while the spherically shaped beads of ammonium nitrate (a solid salt, known in the art as "prills") would be located in the other pocket region, for illustrative purposes the lower pocket region 24. Other examples of materials that can be used for endothermic reactions include salts such as ammonium sulfate, potassium nitrate, sodium nitrate, silver nitrate, ammonium chloride, and ammonium nitrate.

In addition, the reactants 32 and 34 can also include materials that undergo an exothermic reaction upon intermixing, particularly when the structure is used as a hot pack. In one embodiment, for example, super-cooled sodium acetate liquid and sodium acetate crystals (solid), can be used. The super-cooled sodium acetate liquid is stable, but upon activation by the sodium acetate crystals, begins to crystallize and release heat. In this embodiment, the super-cooled sodium acetate liquid would be held in one pocket region, for illustrate purposes the upper pocket region 22, and the sodium acetate crystals would be contained in the other pocket region, for illustrative purposes the lower pocket region 24. In still another embodiment, the reactants can contain iron powder and air (with moisture), which exothermically react when intermixed. Other examples of materials that can be used for exothermal reactants include quick lime, sodium hydroxide, cobalt, chromium, iron hydroxide, magnesium, manganese, molybdenum, tin oxide (II), titanium, sodium, sodium acetate crystals, calcium hydroxide, metallic sodium, magnesium chloride, anhydrous calcium chloride ($CaCl_2$), sodium thiosulfate, and the hydration of zeolites (e.g. sodium aluminosilicates). Other suitable reactants are believed to be described in U.S. Pat. No. 5,792,213 to Bowen and U.S. Pat. No. 6,248,125 to Helming, which are incorporated herein in their entirety by reference thereto for all purposes.

It should be understood that, although the use of two reactants is specifically discussed above, any suitable number of reactants may be utilized in the present invention. For example, in one embodiment, the reactants can include sodium thiosulfate, a solid salt, and glycerine, which when intermixed, produce an exothermic reaction. To incorporate more than two reactants into the laminate structure of the present invention, more than one reactant may be contained within a single pocket region. Moreover, additional substrates and/or inner substrates may be utilized to provide for the formation of additional pocket regions. Moreover, additional substrates may also be used for other reasons as well, such as to limit the mobility of any unbonded regions of the pocket(s).

In accordance with the present invention, the laminate structure is activated by providing a tension force thereto (i.e., stretched and/or wrapped around a body part) that causes the inner substrate to rupture. For example, in some embodiments, a user can apply a tensile force of from about 200 grams force ($g_f$) to about 1000 $g_f$ to rupture a wrap (e.g., 3 inches wide), and in some embodiments, from about 500 $g_f$ to about 1000 $g_f$. Once ruptured, the reactants within the pocket can intermix to produce the desired result. For example, as shown in FIGS. 2 and 4, upon the application of a tension force by a user, the inner substrate 16 ruptures and allows the reactants 32 and 34 within the pocket 22 to intermix. For example, a user can grasp the outer pockets 22 to stretch the entire structure 10 in a longitudinal direction as illustrated by the directional arrow A. Moreover, the structure 10 may also be stretched in a longitudinal direction by wrapping it around an object, such as around the arm or leg of a person. Once stretched, the inner substrate 16 within the pockets 22 ruptures and allows the reactants 32 and 34 to intermix. Thus, a user can beneficially activate the entire laminate structure 10 without having to activate each individual pocket 22. It should be understood, however, that the inner substrate 16 need not rupture within all of the pockets of the laminate structure 10 to provide the desired affect of the present invention.

When the tension force is applied, it is generally desired that the inner substrate 16 rupture before the bonds between the materials are broken and before the outer substrates themselves rupture. Otherwise, the reactants 32 and 34 might undesirably leak out of the laminate structure 10 or prematurely intermix. Thus, in accordance with the present invention, various aspects of the laminate structure can be selectively controlled to ensure that the laminate structure is appropriately activated.

For example, in some embodiments, the strength of the bonds 48, 49, 50, and/or 52 can be selectively controlled to ensure that the inner substrate 16 ruptures only upon activation by a user. For example, in some embodiments, the strength of the bonds 48, 49, 50, and/or 52 can be controlled by controlling the bond width, conditions of bonding (e.g., the length of time bonded, temperature, pressure, etc.), and the like. For example, in one embodiment, the bonds 48, 49, 50, and/or 52 are formed by ultrasonic bonding using a 2 kilowatt plunge bonder at an air pressure of 60 pounds per square inch, a bond time of 300 milliseconds, and a dwell time of 300 milliseconds.

In addition, the materials used to form the inner substrate 16 can also be selected to facilitate the ability of the inner substrate 16 to rupture before the outer substrates 12 and 14 upon application of a tensile force. In some embodiments, films, nonwoven webs, woven fabrics, knitted fabrics, or combinations thereof (e.g., nonwoven fabric laminated to a film), can be used to form the inner substrate 16. When utilized, the films may be formed from a variety of different materials can be utilized. For instance, some suitable thermoplastic polymers used in the fabrication of films can include, but are not limited to, polyolefins (e.g., polyethylene, polypropylene, etc.), including homopolymers, copolymers, terpolymers and blends thereof; ethylene vinyl acetate; ethylene ethyl acrylate; ethylene acrylic acid; ethylene methyl acrylate; ethylene normal butyl acrylate; polyurethane; poly(ether-ester); poly (amid-ether) block copolymers; and the like. In some instances, the thickness of the films may be selected within a certain range to enhance the flexibility of the inner substrate 16. Thus, in some embodiments, the thickness of the films can be less than about 0.05 inches, in some embodiments between about 0.0003 inches to about 0.01 inches, and in some embodiments, between about 0.0007 inches to about 0.02 inches.

As stated above, nonwoven webs can also be utilized. Typically, the nonwoven webs contain synthetic monocomponent or multicomponent fibers. The synthetic fibers may be formed from a variety of thermoplastic polymers. For example, some suitable thermoplastics include, but are not limited, poly(vinyl) chlorides; polyesters; polyamides; polyolefins (e.g., polyethylene, polypropylenes, polybutylenes, etc.); polyurethanes; polystyrenes; poly(vinyl) alcohols; copolymers, terpolymers, and blends of the foregoing; and the like.

In some instances, the basis weight and/or the thickness of the nonwoven webs may be selected within a certain range to enhance the flexibility of the inner substrate 16. Thus, in some embodiments, the thickness of the nonwoven webs can be less than about 0.1 inches, in some embodiments between about 0.005 inches to about 0.06 inches, and in some embodiments, between about 0.015 inches to about 0.03 inches. Moreover, in some embodiments, the basis weight of the nonwoven webs can be less than about 5 ounces per square yard, in some embodiments, between about 0.5 to about 4 ounces per square yard, and in some embodiments, between about 1 to about 2 ounces per square yard.

The inner substrate 16 may also be formed from a laminate material. In one particular embodiment, a nonelastic, laminate may be used. For instance, some suitable nonelastic laminates include, but are not limited to, spunbond/meltblown/spunbond (SMS) and spunbond/meltblown (SM) laminates. An SMS laminate may be made by sequentially depositing onto a moving forming belt first a spunbond fabric layer, then a meltblown fabric layer and last another spunbond layer and then bonding the laminate in a manner described below. Alternatively, the fabric layers may be made individually, collected in rolls, and combined in a separate bonding step. Such SMS laminates are available from Kimberly-Clark Corporation under marks such as Spunguard® and Evolution®. Moreover, SMS materials are described in U.S. Pat. No. 4,041,203 to Brock, et al.; U.S. Pat. No. 5,464,688 to Timmons, et al.; U.S. Pat. No. 4,374,888 to Bornslaeger; U.S. Pat. No. 5,169,706 to Collier, et al.; and U.S. Pat. No. 4,766,029 to Brock, et al., which are also incorporated herein in their entireties by reference thereto for all purposes. Similar to an SMS laminate, an SM laminate is essentially a spunbond layer laminated to a meltblown layer, and can also be used in the present invention.

The permeability of the material used to form the inner substrate 16 can also be selected to optimize various characteristics of the laminate structure 10. For example, it is typically desired that the inner substrate 16 be impermeable to the reactants 32 and 34 so that premature activation does not occur. In particular, when one or more of the reactants contains a liquid, the inner substrate 16 is typically liquid impermeable, such as films formed from polypropylene or polyethylene. Moreover, when one or more of the reactants is a vapor, the inner substrate 16 is typically vapor impermeable.

In some embodiments, the material selected for the inner substrate 16 can actually help control the reaction rate of the reactants 32 and 34 by controlling the degree of intermixing. For example, in some embodiments, vapor permeable, liquid impermeable materials are utilized. Some suitable examples of vapor permeable, liquid-impermeable substrates include, but are not limited to, those described in U.S. Pat. No. 4,828,556 to Braun et al.; U.S. Pat. No. 5,591,510 to Junker et al.; and U.S. Pat. No. 6,156,421 to Stopper, et al., which are incorporated herein in their entirety by reference thereto for all purposes. In one embodiment, the inner substrate 16 can be made from a pre-stretched polymeric film containing fillers, such as calcium carbonate. Depending on the filler size, the extent of prestretching, etc., such films may be formed with pores that are permeable to vapor but impermeable to liquids. When these vapor permeable films are stretched further in accordance with the present invention, the polymer within the film can continue to break away from the filler, thereby rupturing and allowing the reactants 32 and 34 to intermix. Films initially having smaller pore sizes may take longer to become fully permeable to the reactants 32 and 34 than films initially having larger pore sizes. Although not limited in theory, it is believed that, by controlling the initial pore size of the filler-containing film, the rate of reaction of the reactants 32 and 34 can also be better controlled.

The outer substrates 12 and 14 of the laminate structure 10 may also be formed from a variety of different materials. For example, the outer substrates 12 and 14 may be formed from nonwoven webs, woven fabrics, knitted fabrics, or combinations thereof (e.g., nonwoven fabric laminated to a film), such as described above. Typically, the outer substrates 12 and 14 are formed from a material that is impermeable to the particular reactants 32 and 34 to prevent leaking from the laminate structure 10. For example, in one embodiment, the outer substrates 12 and 14 are impermeable to liquids.

To ensure that the outer substrates 12 and 14 do not rupture before the inner substrate 16 when stretched, it is typically desired that the outer substrates 12 and 14 possess some characteristic that enables them to withstand a stretching force that would otherwise rupture the inner substrate 16. For example, in some embodiments, the outer substrates 12 and/or 14 are formed from a material that has a greater tensile strength than the material used to form the inner substrate 16. In other embodiments, the outer substrates 12 and/or 14 are more "extensible" in the direction of stretch than the inner substrate 16. By being more extensible than the inner substrate 16, the outer substrates 12 and/or 14 can better withstand a certain tensile force. As used herein, the term "extensible" generally refers to a material that, when stretched, can at least about 30% in the direction of stretching without substantially rupturing. For example, in some embodiments, outer substrates can be utilized that are capable of being stretched at least about 50%, and in some embodiments, at least about 75% in the direction of stretching without substantially rupturing.

The extensibility of the outer substrates 12 and/or 14 can be enhanced in a variety of different ways. For instance, the outer substrates 12 and/or 14 can have a length that is longer than the inner substrate 16, such as a length 30% greater, in some embodiments 50% greater, and in some embodiments, 75% greater than the length of the inner substrate. In such embodiments, the longer outer substrates can be folded before being bonded to the inner substrate. For example, as shown in FIG. 5, the substrates 12 and 14 each have C-shaped folds 70. However, other folds can be used, such as T-folds, Z-folds, pleated arrangements, corrugations, or other physically arranged elements that are able to extend outwardly, by virtue of change of structural form or arrangement, rather than extension of elastic materials, with respect to their original relaxed configurations. Moreover, additional fold configurations that may be utilized are believed to be described in U.S. Pat. No. 6,149,638 to Vogt, et al., which is incorporated herein in its entirety by reference thereto for all purposes.

Besides being folded, the extensibility of the outer substrates 12 and/or 14 can also be enhanced through other methods. For instance, in some embodiments, the substrates 12 and/or 14 can contain an elastomeric component that includes at least one elastomeric material. When present in a substrate, the elastomeric component can take on various forms. For example, the elastomeric component can make up the entire substrate or form a portion of the substrate. In some embodiments, for instance, the elastomeric component can contain elastic strands or sections uniformly or randomly distributed throughout the substrate. Alternatively, the elastomeric component can be an elastic film or an elastic nonwoven web. The elastomeric component can also be a single layer or a multi-layered material.

In general, any material known in the art to possess elastomeric characteristics can be used in the present invention in the elastomeric component. For example, suitable elastomeric resins include block copolymers having the general formula A—B—A' or A—B, where A and A' are each a thermoplastic polymer endblock which contains a styrenic moiety such as a poly(vinyl arene) and where B is an elastomeric polymer midblock such as a conjugated diene or a lower alkene polymer. Block copolymers for the A and A' blocks, and the present block copolymers are intended to embrace linear, branched and radial block copolymers. In this regard, the radial block copolymers may be designated (A—B)m-X, wherein X is a polyfunctional atom or molecule and in which each (A—B)m-radiates from X in a way that A is an endblock. In the radial block copolymer, X may be an organic or inorganic polyfunctional atom or molecule and m may be an integer having the same value as the functional group originally present in X, which is usually at least 3, and is frequently 4 or 5, but not limited thereto. Thus, the expression "block copolymer," and particularly "A—B—A" and "A—B" block copolymers, can include all block copolymers having such rubbery blocks and thermoplastic blocks as discussed above, which can be extruded (e.g., by meltblowing), and without limitation as to the number of blocks. For example, elastomeric materials, such as (polystyrene/poly(ethylene-butylene)/polystyrene) block copolymers, can be utilized. Commercial examples of such elastomeric copolymers are, for example, those known as KRATON® materials that are available from Shell Chemical Company of Houston, Tex. KRATON® block copolymers are available in several different formulations, a number of which are identified in U.S. Pat. Nos. 4,663,220, 4,323,534, 4,834,738, 5,093,422 and 5,304,599, which are incorporated herein in their entirety by reference thereto for all purposes.

Polymers composed of an elastomeric A—B—A—B tetrablock copolymer may also be used. Such polymers are discussed in U.S. Pat. No. 5,332,613 to Taylor, et al., which is incorporated herein in its entirety by reference thereto for all purposes. In these polymers, A is a thermoplastic polymer block and B is an isoprene monomer unit hydrogenated to substantially a poly(ethylene-propylene) monomer unit. An example of such a tetrablock copolymer is a styrene-poly(ethylene-propylene)-styrene-poly(ethylene-propylene) or S-EP-S-EP elastomeric block copolymer available from the Shell Chemical Company of Houston, Tex. under the trade designation KRATON® G-1657.

Other exemplary elastomeric materials that may be used include polyurethane elastomeric materials such as, for example, those available under the trademark ESTANE® from B. F. Goodrich & Co. or MORTHANE® from Morton Thiokol Corp., and polyester elastomeric materials such as, for example, copolyesters available under the trade designation HYTREL® from E. I. DuPont De Nemours & Company and copolyesters known as ARNITEL®, formerly available from Akzo Plastics of Amhem, Holland and now available from DSM of Sittard, Holland.

Another suitable material is a polyester block amide copolymer having the formula:

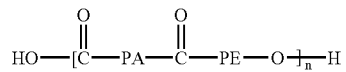

where n is a positive integer, PA represents a polyamide polymer segment and PE represents a polyether polymer segment. In particular, the polyether block amide copolymer has a melting point of from about 150° C. to about 170° C., as measured in accordance with ASTM D-789; a melt index of from about 6 grams per 10 minutes to about 25 grams per 10 minutes, as measured in accordance with ASTM D-1238, condition Q (235C/1 Kg load); a modulus of elasticity in flexure of from about 20 Mpa to about 200 Mpa, as measured in accordance with ASTM D-790; a tensile strength at break of from about 29 Mpa to about 33 Mpa as measured in accordance with ASTM D-638 and an ultimate elongation at break of from about 500 percent to about 700 percent as measured by ASTM D-638. A particular embodiment of the polyether block amide copolymer has a melting point of about 152° C. as measured in accordance with ASTM D-789; a melt index of about 7 grams per 10 minutes, as measured in accordance with ASTM D-1238, condition Q (235 C/1 Kg load); a modulus of elasticity in flexure of about 29.50 Mpa, as measured in accordance with ASTM D-790; a tensile strength at break of about 29 Mpa, as measured in accordance with ASTM D-639; and an elongation at break of about 650 percent, as measured in accordance with ASTM D-638. Such materials are available in various grades under the trade designation PEBAX® from ELF Atochem Inc. of Glen Rock, N.J. Examples of the use of such polymers may be found in U.S. Pat. Nos. 4,724,184, 4,820,572 and 4,923,742 to Killian, which are incorporated herein in their entirety by reference thereto for all purposes.

Elastomeric polymers can also include copolymers of ethylene and at least one vinyl monomer such as, for example, vinyl acetates, unsaturated aliphatic monocarboxylic acids, and esters of such monocarboxylic acids. The elastomeric copolymers and formation of elastomeric nonwoven webs from those elastomeric copolymers are disclosed in, for example, U.S. Pat. No. 4,803,117, which incorporated herein in its entirety by reference thereto for all purposes.

The thermoplastic copolyester elastomers include copolyetheresters having the general formula:

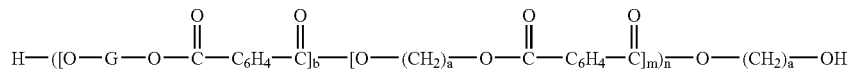

where "G" is selected from the group consisting of poly(oxyethylene)-alpha, omega-diol, poly(oxypropylene)-alpha, omega-diol, poly(oxytetramethylene)-alpha, omega-diol and "a" and "b" are positive integers including 2, 4 and 6, "m" and "n" are positive integers including 1–20. Such materials generally have an elongation at break of from about 600 percent to 750 percent when measured in accordance with ASTM D-638 and a melt point of from about 350° F. to about 400° F. (176 to 205° C.) when measured in accordance with ASTM D-2117.

In addition, some examples of suitable elastomeric olefin polymers are available from Exxon Chemical Company of Baytown, Tex. under the trade name ACHIEVE® for polypropylene based polymers and EXACT® and EXCEED® for polyethylene based polymers. Dow Chemical Company of Midland, Mich. has polymers commercially available under the name ENGAGE®. These materials are believed to be produced using non-stereoselective metallocene catalysts. Exxon generally refers to their metallocene catalyst technology as "single site" catalysts, while Dow refers to theirs as "constrained geometry" catalysts under the name INSIGHT® to distinguish them from traditional Ziegler-Natta catalysts that have multiple reaction sites.

When incorporating an elastomeric component containing an elastomeric material, such as described above, into a substrate, it is sometimes desired that the elastomeric component be an elastic laminate that contains an elastomeric material with one or more other layers, such as foams, films, apertured films, and/or nonwoven webs. An elastic laminate generally contains layers that can be bonded together so that at least one of the layers has the characteristics of an elastic polymer. The elastic material used in the elastic laminates can be made from materials, such as described above, that are formed into films, such as a microporous film, fibrous webs, such as a web made from meltblown fibers, spunbond fibers, foams, and the like.

For example, in one embodiment, the elastic laminate can be a "neck-bonded" laminate. A "neck-bonded" laminate refers to a composite material having at least two layers in which one layer is a necked, non-elastic layer and the other layer is an elastic layer. The resulting laminate is thereby a material that is elastic in the cross-direction. Some examples of neck-bonded laminates are described in U.S. Pat. Nos. 5,226,992, 4,981,747, 4,965,122, and 5,336,545, all to Morman, which are incorporated herein in their entirety by reference thereto for all purposes.

The elastic laminate can also be a "stretch-bonded" laminate, which refers to a composite material having at least two layers in which one layer is a gatherable layer and in which the other layer is an elastic layer. The layers are joined together when the elastic layer is in an extended condition so that upon relaxing the layers, the gatherable layer is gathered. For example, one elastic member can be bonded to another member while the elastic member is extended at least about 25 percent of its relaxed length. Such a multilayer composite elastic material may be stretched until the nonelastic layer is fully extended.

For example, one suitable type of stretch-bonded laminate is a spunbonded laminate, such as disclosed in U.S. Pat. No. 4,720,415 to Vander Wielen, et al., which is incorporated herein in its entirety by reference thereto for all purposes. Another suitable type of stretch-bonded laminate is a continuous filament spunbonded laminate, such as disclosed in U.S. Pat. No. 5,385,775 to Wright, which is incorporated herein in its entirety by reference thereto for all purposes. For instance, Wright discloses a composite elastic material that includes: (1) an anisotropic elastic fibrous web having at least one layer of elastomeric meltblown fibers and at least one layer of elastomeric filaments autogenously bonded to at least a portion of the elastomeric meltblown fibers, and (2) at least one gatherable layer joined at spaced-apart locations to the anisotropic elastic fibrous web so that the gatherable layer is gathered between the spaced-apart locations. The gatherable layer is joined to the elastic fibrous web when the elastic web is in a stretched condition so that when the elastic web relaxes, the gatherable layer gathers between the spaced-apart bonding locations. Other composite elastic materials are described and disclosed in U.S. Pat. No. 4,789,699 to Kieffer et al., U.S. Pat. No. 4,781,966 to Taylor, U.S. Pat. No. 4,657,802 to Morman, and U.S. Pat. No. 4,655,760 to Morman et al., which are incorporated herein in their entirety by reference thereto for all purposes.

In one embodiment, the elastic laminate can also be a necked stretch bonded laminate. As used herein, a necked stretch bonded laminate is defined as a laminate made from the combination of a neck-bonded laminate and a stretch-bonded laminate. Examples of necked stretch bonded laminates are disclosed in U.S. Pat. Nos. 5,114,781 and 5,116,662, which are both incorporated herein in their entirety by reference thereto for all purposes. Of particular advantage, a necked stretch bonded laminate can be stretchable in both the machine and cross-machine directions.

As indicated above, the laminate structures of the present invention can be used to form hot or cold wraps, which are configured to be placed adjacent to the body part of a user to provide the desired heating or cooling effect. Hot or cold wraps can generally have any desired shape or size. For example, the wrap can be oval-shaped, circular in shape, or rectangular in shape with or without rounded corners. To activate the hot or cold wrap, a user can simply stretch it in a longitudinal direction (e.g., wrap around a body part) until the inner substrates ruptures. Thereafter, the reactants can mix to cause the desired reaction.

Although the embodiments described above typically relate to configurations that are designed to inhibit leakage or removal of the reactants from the laminate structure, it may be sometimes desired that such reactants be removable by a user. For instance, in one embodiment, a user can tear or cut the laminate structure to remove reactants that have been mixed together. In other embodiments, the substrates may be rupturable and/or permeable to allow removal of the reactants therefrom.

The present invention may be better understood with reference to the following example.

EXAMPLE 1

The ability to form a single-pocketed laminate structure that can rupture to activate the mixing of multiple materials was demonstrated. Initially, a 4×9 cm laminate structure was formed with a single pocket having an upper and lower pocket region. An inner layer separated the two pocket regions such that two (2) grams of salt were contained within the upper pocket region and two (2) grams of pepper were contained within the lower pocket region.

The inner layer was a filled polyethylene film having a thickness of 0.025 millimeters. The inner layer had a length of 4 centimeters and a width of 9 centimeters. The tensile strength of the film was approximately 25 MPa as determined according to ASTM D-5035-95. The elongation to break of the film was 20% such that the film would rupture after being extended approximately 0.8 centimeters.

The outer layers of the structure were formed from a polyethylene film. These layers were folded during assembly such that the length of the structure (i.e., 4 centimeters) was 50% of the unfolded length of the outer layers (i.e., 8 centimeters). The length contained in the fold (which is equal to the length of the outer layers minus the resulting length of the structure) was equal to 4 centimeters, which was greater than the elongation-to-break of the inner layer, i.e., 0.8 centimeters.

When bonded to the inner barrier layer, the folds of the outer layers were held by the bonds orthogonal to the folds. The layers were ultrasonically bonded together using a Model 920 iw Bransen plunge bonder (2 kilowatt). The bonding time was 300 milliseconds with a hold time of 300 milliseconds. The bonding pressure was 60 pounds per square inch. A 6"×1" smooth horn was used with a 6"×0.25" female knurled anvil.

To activate the laminate structure, a tensile force was applied in the longitudinal direction such that the folds of the outer layers partially unfolded. As the outer layers unfolded, the inner layer, which had no folds, ruptured under tension after being extended 0.8 centimeters. The outer layers extended 4 centimeters (100% of their initial folded length) upon stretching. When the inner layer ruptured, the salt and pepper mixed together.

EXAMPLE 2

The ability to form a single-pocketed laminate structure that can rupture to activate the mixing of multiple materials was demonstrated. Initially, a 10.5×11 cm laminate structure was formed with a single pocket having an upper and lower pocket region. An inner layer separated the two pocket regions such that five (5) grams of salt were contained within the upper pocket region and five (5) grams of pepper were contained within the lower pocket region.

The inner layer was a filled polyethylene film having a thickness of 0.025 millimeters. The inner layer had a length of 10.5 centimeters and a width of 11 centimeters. The tensile strength of the film was approximately 25 MPa as determined according to ASTM D-5035-95. The elongation to break of the film was 20% such that the film would break after being extended approximately 2.1 centimeters.

The outer layers of the structure were formed from a polyethylene film. These layers were folded during assembly such that the length of the structure (i.e., 10.5 centimeters) was 78% of the unfolded length of the outer layers (i.e., 13.5 centimeters). The length contained in the fold (which is equal to the length of the outer layers minus the resulting length of the structure) was equal to about 3 centimeters, which was greater than the elongation-to-break of the inner layer, i.e., 2.1 centimeters.

When bonded to the inner barrier layer, the folds of the outer layers were held by the bonds orthogonal to the folds. The layers were ultrasonically bonded together using a Model 920 iw Bransen plunge bonder (2 kilowatt). The bonding time was 300 milliseconds with a hold time of 300 milliseconds. The bonding pressure was 60 pounds per square inch. A 6"×1" smooth horn was used with a 6"×0.25" female knurled anvil.

To activate the laminate structure, a tensile force was applied in the longitudinal direction such that the folds of the outer layers partially unfolded. As the outer layers unfolded, the inner layer, which had no folds, ruptured under tension after being stretched 2.1 centimeters. The outer layers extended 3 centimeters (29% of their initial folded length) upon stretching. When the inner layer ruptured, the salt and pepper mixed together.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A laminate structure comprising:
   an inner substrate that ruptures upon the application of a tensile force in a longitudinal direction;
   extensible first and second outer substrates, wherein said inner substrate is positioned between and bonded to said first and said second outer substrates to define at least one pocket having an upper pocket region formed from the first outer substrate and a lower pocket region formed from the second outer substrate, wherein said tensile force does not cause said first and said second substrates to substantially rupture;
   a first reactant contained within said upper pocket region; and
   a second reactant contained within said lower pocket region, wherein said first reactant and said second reactant are intermixed when said inner substrate is ruptured, said intermixing causing said reactants to undergo an endothermic or exothermic reaction.

2. A laminate structure as defined in claim 1, wherein said first and said second outer substrates are selected from the group consisting of nonwoven webs, films, woven fabrics, knitted fabrics and combinations thereof.

3. A laminate structure as defined in claim 1, wherein at least one of said outer substrates contains a film.

4. A laminate structure as defined in claim 1, wherein at least one of said outer substrates contains a nonwoven web.

5. A laminate structure as defined in claim 1, wherein at least one of said extensible outer substrates contains an elastomeric material.

6. A laminate structure as defined in claim 1, wherein at least one of said extensible outer substrates has a length greater than the length of said inner substrate.

7. A laminate structure as defined in claim 6, wherein at least one of said extensible outer substrates is folded.

8. A laminate structure as defined in claim 1, wherein said outer substrates are capable of extending at least about 30% in said longitudinal direction.

9. A laminate structure as defined in claim 1, wherein said outer substrates are capable of extending at least about 50% in said longitudinal direction.

10. A laminate structure as defined in claim 1, wherein said outer substrates are capable of extending at least about 75% in said longitudinal direction.

11. A laminate structure as defined in claim 1, wherein said inner substrate is selected from the group consisting of nonwoven webs, films, woven fabrics, knitted fabrics and combinations thereof.

12. A laminate structure as defined in claim 1, wherein said inner substrate contains a film.

13. A laminate structure as defined in claim 12, wherein said film is prestretched and contains a filler.

14. A laminate structure as defined in claim 1, wherein said inner substrate is impermeable to said first reactant and said second reactant.

15. A laminate structure as defined in claim 1, wherein two longitudinal edges and one transverse edge of said first substrate and said second substrate are bonded together.

16. A laminate structure as defined in claim 15, wherein said inner substrate is also bonded to said two longitudinal edges and said transverse edge of said first and said second outer substrates.

17. A laminate structure as defined in claim 16, wherein said inner substrate remained unbonded to an additional transverse edge of said first and said second outer substrates.

18. A laminate structure as defined in claim 16, wherein said bonds between said outer substrates and between said outer substrates and said inner substrate do not break upon application of said tensile force.

19. A laminate structure as defined in claim 1, wherein said laminate structure comprises multiple pockets.

20. A laminate structure as defined in claim 1, wherein at least a portion of said multiple pockets are aligned in series.

21. A wrap comprising:
    an inner substrate that ruptures upon the application of a tensile force in a longitudinal direction;
    a first and second outer substrate that extend at least about 30% in said longitudinal direction upon application of said tensile force without substantially rupturing, wherein said inner substrate is positioned between and bonded to said first and said second outer substrates to define multiple pockets aligned in series, wherein each of said pockets has an upper pocket region formed from the first outer substrate and a lower pocket region from the second outer substrate;
    a first reactant contained within said upper pocket region of at least a portion of said pockets; and
    a second reactant contained within said lower pocket region of said pockets that also contain said first reactant, wherein said first reactant and said second reactant are intermixed when said inner substrate is ruptured, said intermixing causing said reactants to undergo an endothermic or exothermic reaction.

22. A wrap as defined in claim 21, wherein said outer substrates contain a film, a nonwoven web, or combinations thereof.

23. A wrap as defined in claim 21, wherein at least one of said outer substrates contains an elastomeric material.

24. A wrap as defined in claim 21, wherein at least one of said outer substrates is folded.

25. A wrap as defined in claim 21, wherein said outer substrates are capable of extending at least about 50% in said longitudinal direction upon application of said tensile force.

26. A wrap as defined in claim 21, wherein said outer substrates are capable of extending at least about 75% in said longitudinal direction upon application of said tensile force.

27. A wrap as defined in claim 21, wherein said inner substrate contains a film.

28. A wrap as defined in claim 21, wherein two longitudinal edges and one transverse edge of said first substrate and said second substrate are bonded together.

29. A wrap as defined in claim 28, wherein said inner substrate is also bonded to said two longitudinal edges of said first and said second outer substrates.

30. A wrap as defined in claim 29, wherein said inner substrate remained unbonded to an additional transverse edge of said first and said second outer substrates.

31. A laminate structure as defined in claim 1, wherein said intermixing causes said reactants to undergo an exothermic reaction.

32. A laminate structure as defined in claim 1, wherein said intermixing causes said reactants to undergo an endothermic reaction.

33. A wrap as defined in claim 21, wherein said intermixing causes said reactants to undergo an exothermic reaction.

34. A wrap as defined in claim 21, wherein said intermixing causes said reactants to undergo an endothermic reaction.

* * * * *